(12) United States Patent
Niiyama

(10) Patent No.: US 8,747,632 B2
(45) Date of Patent: Jun. 10, 2014

(54) BLOOD MEASURING APPARATUS

(75) Inventor: Yoshihiro Niiyama, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 13/323,626

(22) Filed: Dec. 12, 2011

(65) Prior Publication Data

US 2012/0145536 A1     Jun. 14, 2012

(30) Foreign Application Priority Data

Dec. 13, 2010   (JP) ................. 2010-276909

(51) Int. Cl.
| | | |
|---|---|---|
| *A61B 5/145* | (2006.01) | |
| *A61B 5/1468* | (2006.01) | |
| *C25C 7/06* | (2006.01) | |
| *A61L 2/03* | (2006.01) | |
| *G01N 33/49* | (2006.01) | |

(52) U.S. Cl.
CPC ............... *A61B 5/1468* (2013.01); *C25C 7/06* (2013.01); *A61L 2/035* (2013.01); *G01N 33/49* (2013.01)
USPC ..................................... 204/229.2; 73/864.81

(58) Field of Classification Search
CPC .... A61B 5/1459; A61B 5/1473; A61B 5/145; A61B 5/1468; A61L 2/18; A61L 2/035; A61L 2202/17; C25C 7/06; G01N 15/02; G01N 15/12; G01N 15/1218; G01N 33/49
USPC ............. 204/403.01, 409, 229.4–229.7; 422/68.1, 73; 73/864.81–864.83; 436/43, 54, 66, 826
See application file for complete search history.

(56) References Cited

U.S. PATENT DOCUMENTS

| | | | | |
|---|---|---|---|---|
| 2,656,508 A | | 10/1953 | Coulter | |
| 5,023,054 A | * | 6/1991 | Sato et al. | ............ 422/82.09 |
| 6,084,392 A | | 7/2000 | Shine et al. | |

FOREIGN PATENT DOCUMENTS

| | | |
|---|---|---|
| CN | 201497691 U | 6/2010 |
| JP | 11-153604 A | 6/1999 |
| JP | 2000-502796 A | 3/2000 |
| JP | 2000-334460 A | 12/2000 |

OTHER PUBLICATIONS

Chinese Office Action for the related Chinese Patent Application No. 201110415449.0 dated Jan. 6, 2014.

* cited by examiner

*Primary Examiner* — J. Christopher Ball
(74) *Attorney, Agent, or Firm* — Kenealy Vaidya LLP

(57) ABSTRACT

A blood measuring apparatus includes: first and second chambers which communicate with each other through an aperture; first and second electrodes which are disposed respectively in the first chamber and the second chamber; and a controller: which performs blood measurement by causing a current to flow between the first and second electrodes in a state where diluted blood is contained in the first chamber and diluting solution is contained in the second chamber; and which performs electrolysis by applying a voltage between the first and second electrodes in a state where diluting solution is contained in the first and second chambers, thereby producing washing solution, and which performs washing on at least the aperture, and the first and second chambers by using the produced washing solution.

12 Claims, 5 Drawing Sheets

BLOOD MEASURING APPARATUS

BACKGROUND OF THE INVENTION

The present invention relates to a blood measuring apparatus using the electrical resistance method.

There is a blood cell counting apparatus using the electrical resistance method. Such an apparatus includes first and second chambers which communicate with each other through an aperture, in each of which diluted blood for measurement is contained, and in which electrodes are disposed respectively in the two chambers, and performs the blood cell counting (see U.S. Pat. No. 2,656,508).

In the apparatus, proteins in blood adhere to the aperture and the interiors of the first and second chambers. Whereby, the wettability is impaired particularly in the aperture and air bubbles adhere to the aperture. In such a case, the air bubbles are caused to function as a disturbance in measurement by fluid vibration, and therefore it is impossible to obtain an adequate measurement result. When air bubbles once adhere to the vicinity of the aperture, moreover, the air bubbles are hardly removed by a water stream.

Therefore, the aperture and chambers are washed with chlorinated detergent for proteins decomposition which is sucked from the outside of the measuring apparatus. However, the expiration is set in chlorinated detergent because of the property that, when chlorinated detergent comes in contact with the air, the detergent decomposes, and hence management of such detergent is cumbersome. In some countries, import restrictions are imposed on chlorinated detergent. In the case where a measuring apparatus is additionally provided with chlorinated detergent, for example, the importation of the apparatus itself is restricted.

Alternatively, enzymatic detergent may be used in such washing. In the case where enzymatic detergent is used, however, washing must be performed in the state where the liquid temperature is held at a constant temperature, thereby causing a problem in that such washing requires a prolonged period of time.

Also in an apparatus which measures biological fluid other than blood, in the case where adhering materials such as proteins are to be washed away, usually, a similar problem arises.

Furthermore, there is an automatic analyzing apparatus in which a washing solution is produced by electrolysis of a saline solution, and a reaction chamber is washed (see JP-A-11-153604).

SUMMARY

It is therefore an object of the invention to provide a blood measuring apparatus in which, by using chambers of a blood measuring apparatus, a required washing solution can be produced and adequate washing can be performed.

In order to achieve the object, according to the invention, there is provided a blood measuring apparatus comprising: first and second chambers which communicate with each other through an aperture; first and second electrodes which are disposed respectively in the first chamber and the second chamber; and a controller: which performs blood measurement by causing a current to flow between the first and second electrodes in a state where diluted blood is contained in the first chamber and diluting solution is contained in the second chamber; and which performs electrolysis by applying a voltage between the first and second electrodes in a state where diluting solution is contained in the first and second chambers, thereby producing washing solution, and which performs washing on at least the aperture, and the first and second chambers by using the produced washing solution.

The blood measuring apparatus may further comprise an inputting unit through which a washing instruction is to be given. When the controller receives the washing instruction, the controller may produce the washing solution and perform the washing by using the produced washing solution.

The controller may detect a time when washing is necessary. When the controller detects the time, the controller may produce the washing solution and perform the washing by using the produced washing solution.

The controller may produce the washing solution and perform the washing by using the produced washing solution at a predetermined time.

The washing solution may include a first washing solution produced in the first chamber and a second washing solution produced in the second chamber, and the controller may perform washing using one of the first washing solution and the second washing solution.

The controller may set at least one of an applied voltage, a time length of voltage, and a polarity.

DETAILED DESCRIPTION OF EMBODIMENTS

Figure 1:
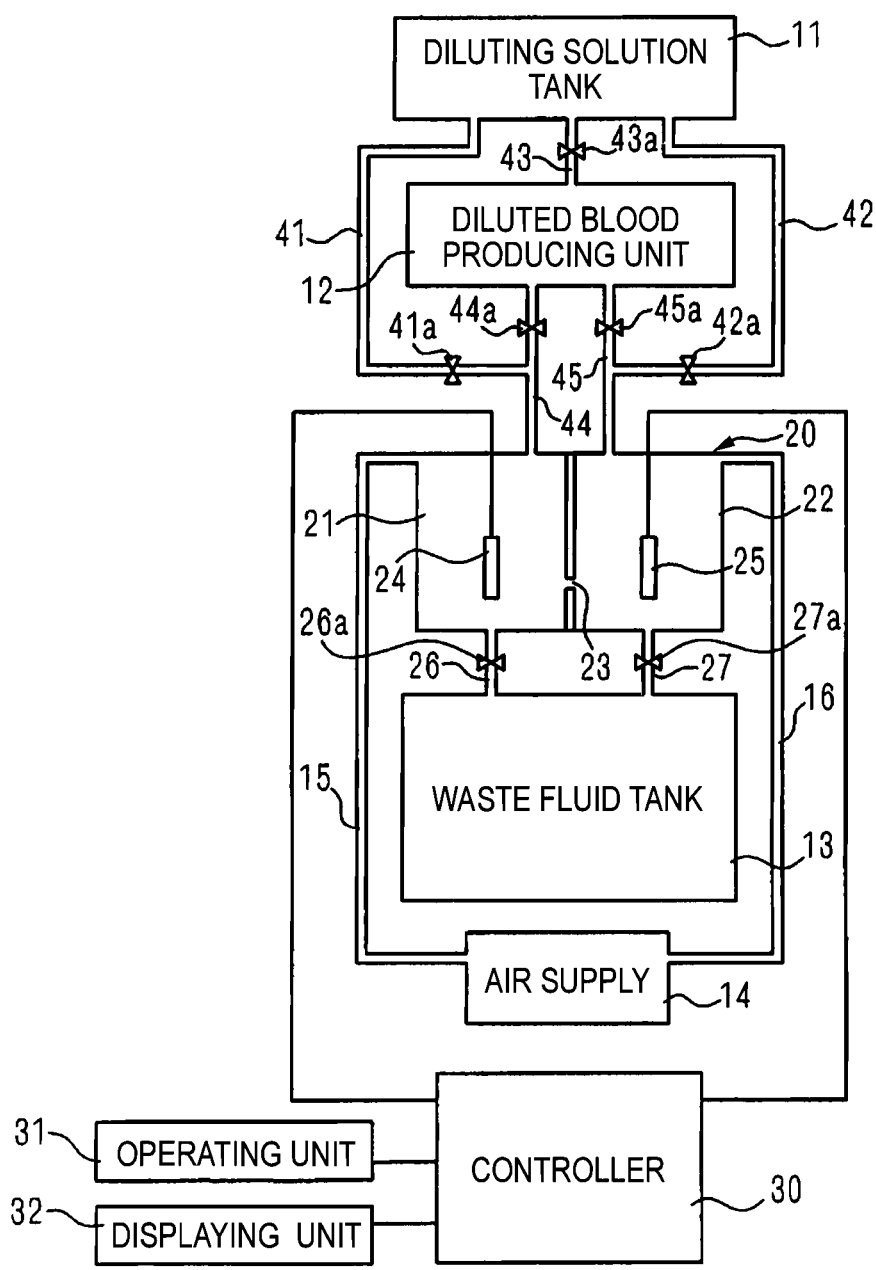
FIG. 1 is a block diagram of an embodiment of the blood measuring apparatus of the invention.

Hereinafter, an embodiment of the blood measuring apparatus of the invention is described with reference to the accompanying drawings. In the figures, the identical components are denoted by the same reference numerals, and duplicate description will be omitted. FIG. 1 shows a block diagram of the embodiment of the blood measuring apparatus. The apparatus measures blood cell count by using the electrical resistance method.

The blood measuring apparatus includes components such as a diluting solution tank 11, a diluted blood producing unit 12, a chamber 20 including a first chamber 21 and a second chamber 22, a waste fluid tank 13, an air supply 14, and a controller 30.

The diluting solution tank 11 supplies a diluting solution (physiologic saline) to the first chamber 21 through a supply path 41, and supplies the diluting solution to the second chamber 22 through a supply path 42. At this time, the controller 30 controls opening and closing of valves 41a, 42a.

The diluted blood producing unit 12 produces diluted blood under the control of the controller 30, receives a supply of blood, which is a specimen, from the outside through a capillary tube, takes in the diluting solution from the diluting solution tank 11 through a flow path 43, and produces diluted blood of a predetermined concentration.

Under the control of the controller 30, the diluted blood producing unit 12 supplies the diluted blood to the first chamber 21 through a flow path 44.

The first chamber 21 and the second chamber 22 are communicated with each other through an aperture 23, and a first electrode 24 and a second electrode 25 are opposed to each other across the aperture 23. The first electrode 24 and the second electrode 25 are connected to the controller 30.

The first chamber 21 and the waste fluid tank 13 are coupled with each other through a flow path 26, and the second chamber 22 and the waste fluid tank 13 are coupled with each other through a flow path 27. The controller 30 controls the valves 26a, 27a so as to discharge the liquids in the first and second chambers 21, 22 into the waste fluid tank 13.

The air supply 14 is connected to the first chamber 21 through a pipe 15, and to the second chamber 22 through a pipe 16. The controller 30 controls the air supply 14 so as to suck and exhaust the air into and from the first chamber 21 through the pipe 15, and into and from the second chamber 22 through the pipe 16.

An operating unit 31 including various keys, and a displaying unit 32 including LEDs and the like are connected to the controller 30. The controller 30 performs the above-described controls, and controls the measurement of blood cells, the production of the washing solution, and the washing process.

In the state where the diluted blood is contained in the first chamber 21 and the diluting solution is contained in the second chamber 22, the controller 30 causes a minute current to flow between the first and second electrodes 24, 25 to perform the blood measurement. Namely, when the minute current flows between the first and second electrodes 24, 25, the controller 30 detects the resistance which is changed by the existence of blood cells passing through the aperture 23, as a voltage, and counts the blood cells in accordance with the detected voltage.

In the state where the diluting solution is contained in the first chamber 21 and the second chamber 22, the controller 30 applies a voltage (the voltage value and the polarity can be arbitrarily set) between the first and second electrodes 24, 25 to perform electrolysis, thereby producing a washing solution. Since the diluting solution is physiologic saline, acidic water (hypochlorous water) having washing and sterilizing effects is produced on the side of the anode of the second electrode 25, and alkaline water having a sterilizing effect is produced on the side of the cathode of the first electrode 24. In the process of producing the washing solution, the aperture 23 functions as a diaphragm which allows ions to pass therethrough but inhibits movement of liquids. Without using a special film such as an ion permeation film, therefore, it is possible to produce acidic and alkaline waters of a high concentration. Specifically, as a result of energization under a voltage of 20 V and a current of about 1 mA, high acidic water of pH 2 was produced in the anode chamber, and high alkaline water of pH 12 was produced in the cathode chamber.

As described above, the blood measuring apparatus operator may set at least one of the applied voltage, the time length of voltage, and the polarity. Alternatively, "ordinary washing mode (washing by low alkaline water or low acid water)" and "strong washing mode (washing by high alkaline water or high acid water)" of different time length of voltage may be prepared and adequately selected.

The controller 30 performs washing on at least the aperture 23, and the first and second chambers 21, 22 while using the thus produced washing solution.

The operating unit 31 includes a measurement start switch, and a washing start switch through which a washing instruction is to be given. The washing start switch is inputting means for giving the washing instruction. Upon receiving the washing instruction given through the washing start switch, the controller 30 performs washing while using the thus produced washing solution. The controller 30 detects a time when washing is necessary, and performs washing using the thus produced washing solution.

Figure 2:
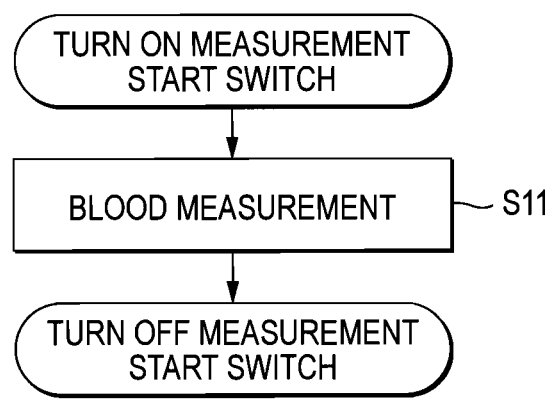
FIG. 2 is a flowchart illustrating the operation of the blood measuring apparatus of the invention.
Figure 3:
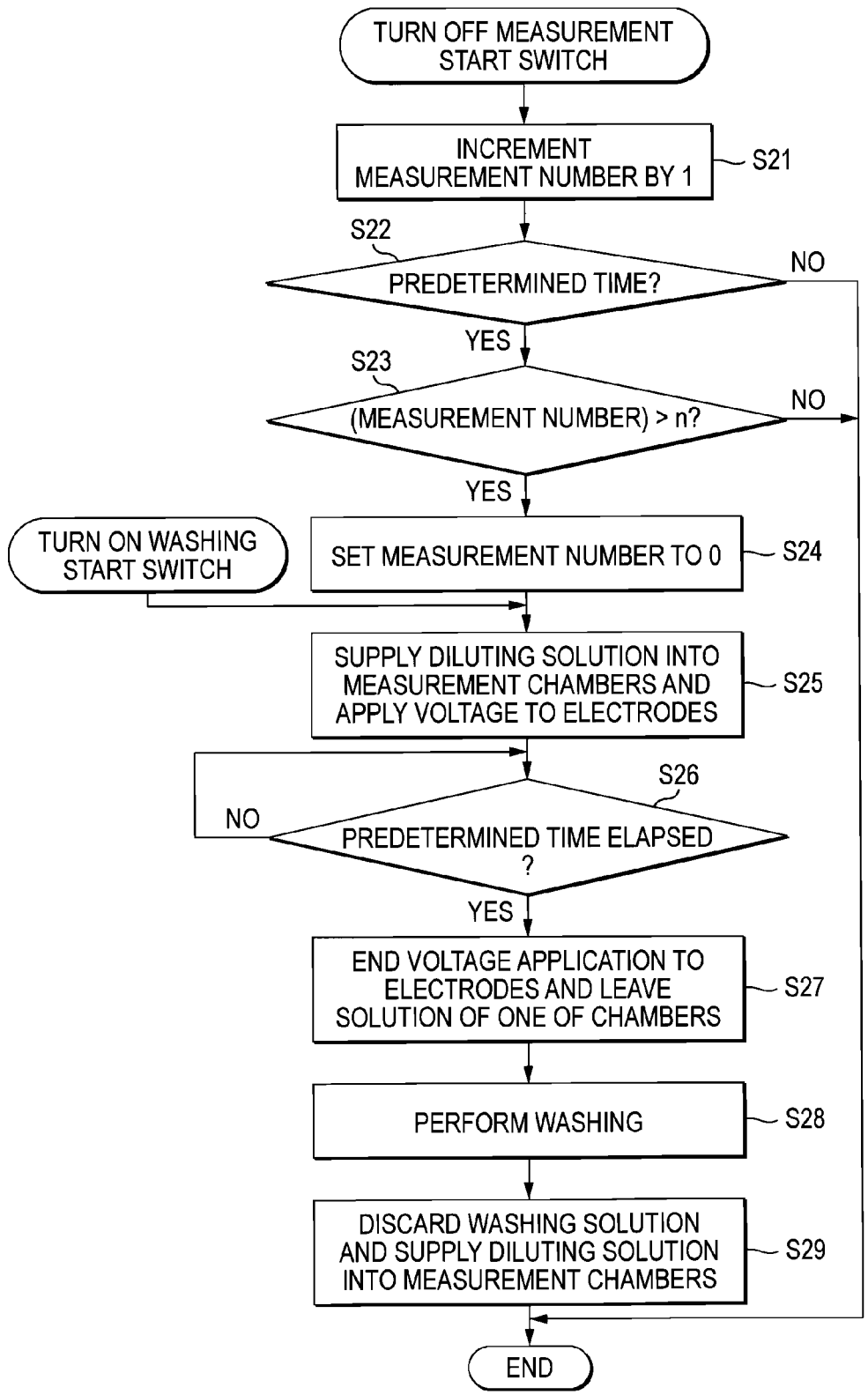
FIG. 3 is a flowchart illustrating the operation of the blood measuring apparatus of the invention.

In the blood measuring apparatus which is configured as described above, the controller 30 performs a measurement process by a program corresponding to the flowchart of FIG. 2, and an operation of producing the washing solution and washing based on the flowchart of FIG. 3. The operation will be described.

When the measurement start switch is turned on, the controller 30 causes a minute current to flow between the first and second electrodes 24, 25 to perform the blood measurement (S11). The displaying unit 32 displays a result of the measurement. When the measurement start switch is turned off, the measurement is ended.

When the measurement start switch is turned off, the measurement number is incremented by one, the resulting number is held in a register (S21), and it is detected whether it is a predetermined time or not (S22). Usually, the predetermined time may be set to a desired time such as night time when measurement is not performed. If it is determined as NO in step S22, the process is ended, and, if it is determined as YES, it is checked whether the measurement number is larger than a predetermined number n or not (S23). The predetermined number n may be set to a number by which it is estimated that proteins or the like adhere to the interior of the chamber 20 at a degree that adversely affects the measurement result.

If it is detected in step S23 that the measurement number is equal to or smaller than the predetermined number n, the process is ended. If the measurement number is larger than the predetermined number n, the measurement number held in the register is set to 0 (S24), and the process proceeds to step S25. Also when the washing start switch is turned on, the process proceeds to step S25, and the controller 30 produces the washing solution and performs washing using the produced washing solution.

In step S25, the controller 30 controls the valves 41a, 42a so as to flow the diluting solution from the diluting solution tank 11 into the first and second chambers 21, 22, and applies a voltage to the first and second electrodes 24, 25 to perform electrolysis, thereby producing the washing solution (S25). It is detected whether the voltage is applied for the predetermined time or not (S26), and the washing solution of a desired concentration is produced.

If elapse of the predetermined time is detected in step S26, the voltage applied to the first and second electrodes 24, 25, are stopped and the valves 26a, 27a are controlled so that the washing solution in one of the first and second chambers 21, 22 remains. In the case where washing using the acidic water, and that using the alkaline water are to be performed, after the end of step S29, the process returns to step S25, the washing solution is produced, and the washing solution which is different from that in the first time remains.

Figure 4A:
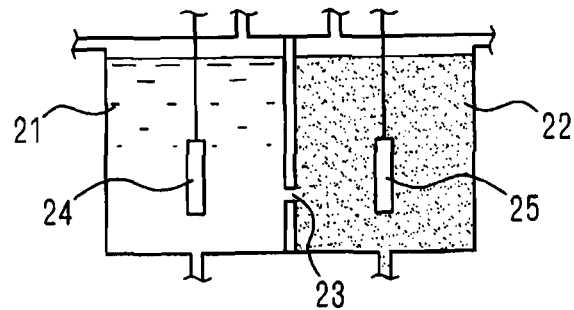
FIGS. 4A to 4D are process flow charts illustrating the operation of the blood measuring apparatus of the invention.
Figure 4B:
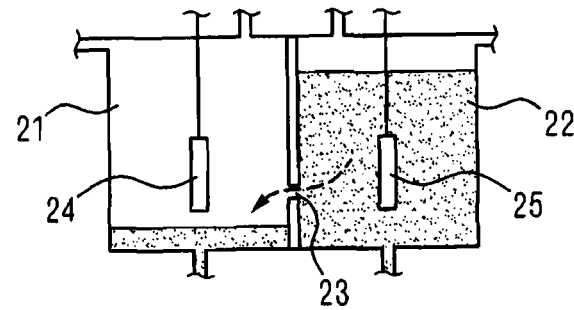
Figure 4C:
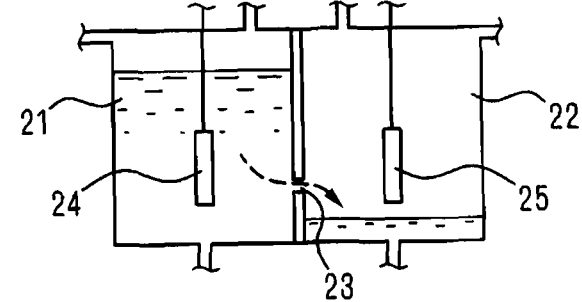

In succession to step S27, washing is performed in step S28. In the case where the washing solution is produced while setting the first electrode 24 as the cathode, and the second electrode 25 as the anode, for example, alkaline water is produced in the first chamber 21, and acidic water is produced in the second chamber 22 as shown in FIG. 4A. In the case where the alkaline water produced in the first chamber 21 is to remain, then, the valve 27a is opened in a state where the valve 26a is closed, thereby discharging the acidic water in the second chamber 22. Next, in a state where the valves 26a, 27a are closed, the air supply 14 is controlled so as to suck the air into the pipe 16 and exhaust the air from the pipe 15, thereby moving the alkaline water produced in the first chamber 21 to the second chamber 22 through the aperture 23 as shown in FIG. 4C. After elapse of a constant time, the air supply 14 is further controlled so as to suck the air into the pipe 15 and exhaust the air from the pipe 16, thereby moving the alkaline water in the direction which is opposite to that in the above. The movement of the alkaline water is repeated several times, and then washing and sterilization are completed.

In the case where the acidic water produced in the second chamber 22 is to remain, in a state where the valve 27a is closed in the state of FIG. 4A, the valve 26a is opened to discharge the alkaline water in the first chamber 21. Next, in a state where the valves 26a, 27a are closed, the air supply 14 is controlled so as to suck the air into the pipe 15 and exhaust the air from the pipe 16, thereby moving the acidic water to the first chamber 21 through the aperture 23 as shown in FIG. 4B. After elapse of a constant time, the air supply 14 is further controlled so as to suck the air into the pipe 16 and exhaust the air from the pipe 15, thereby moving the acidic water in the direction which is opposite to that in the above. The movement of the acidic water is repeated several times, and then sterilization is completed.

Figure 4D:
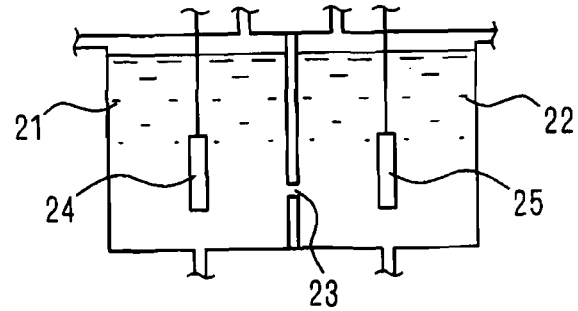

When the washing and sterilizing process of step S28 is ended, the valves 26a, 27a are opened and the washing solution is discarded into the waste fluid tank 13. Thereafter, the valves 26a, 27a are closed, the valves 41a, 42a are opened, the diluting solution is caused to flow from the diluting solution tank 11 into the first and second chambers 21, 22 to attain the state shown in FIG. 4D, and the operation is ended.

Figure 5:
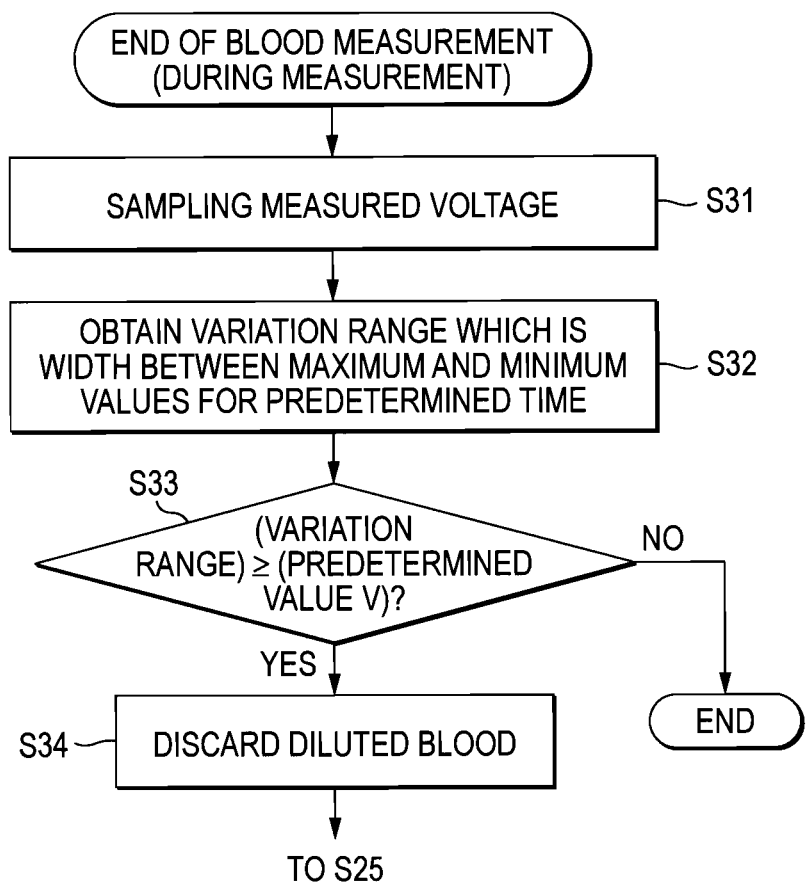
FIG. 5 is a flowchart illustrating the operation of the blood measuring apparatus of the invention.

FIG. 5 shows an example in which, in place of the detection in which a time when washing is necessary is detected by using the measurement number, a time when washing is necessary is detected by using the measurement result, in the form of a flowchart. After the end of the blood measurement (or during the measurement), the measured voltage is sampled (S31), the variation range which is the width between the maximum and minimum values of the variation for a predetermined time is obtained (S32), and it is detected whether the variation range is equal to or larger than a predetermined value V or not (S33). If the variation range is smaller than the predetermined value V, the process is ended, and, if the variation range is equal to or larger than the predetermined value V, the diluted blood in the first and second chambers 21, 22 is discarded (S34), and the process proceeds to step S25 of FIG. 3. The subsequent process is performed as described above.

As described above, according to the embodiment, by using the chambers of the blood measuring apparatus, a required washing solution can be produced and adequate washing can be performed without using an expensive ion permeation film or the like.

According to an aspect of the invention, since the washing solution is produced by using the first and second chambers in which diluted blood is to be contained, and the electrodes, it is not required to additionally dispose a chamber or configuration for producing the washing solution. Therefore, the size of the apparatus can be reduced, and the production cost can be lowered. In the electrolysis, the aperture exerts a function of allowing ions to pass therethrough, but impeding the movement of liquid. Therefore, it is not required to additionally dispose an expensive diaphragm for ion passage, and it is possible to obtain a washing solution having a pH value which is necessary for washing.

According to an aspect of the invention, when receiving the washing instruction from the inputting unit through which the washing instruction is given, the production of the washing solution and washing using the washing solution are performed. Therefore, washing can be performed at a desired timing, and the apparatus is convenient for use. According to an aspect of the invention, a time when washing is necessary is detected, and the production of the washing solution, and washing using the washing solution are performed. Therefore, washing is automatically performed at a required timing, and the apparatus is convenient for use.

According to an aspect of the invention, the production of the washing solution, and washing using the washing solution are performed at a predetermined time. Therefore, washing is performed at a time when measurement is not conducted, such as night time, and the apparatus is convenient for use.

According to an aspect of the invention, washing using the washing solution which is produced in one of the first chamber and the second chamber is performed. Therefore, washing can be adequately performed by using a chlorinated washing solution or an alkaline solution.

According to an aspect of the invention, since the controller can arbitrarily set at least one of the application voltage, the application time, and the polarity, the concentration of the washing solution can be changed.

What is claimed is:

1. A blood measuring apparatus comprising:
   first and second chambers which communicate with each other through an aperture;
   first and second electrodes which are disposed respectively in the first chamber and the second chamber;
   a diluting solution tank connected separately to each of the first and second chambers;
   a diluted blood producing unit connected to the diluting solution tank wherein blood and a diluting solution are combined to produce diluted blood and connected separately to each of the first and second chambers;
   a controller in communication with the first and second chambers, first and second electrodes, the diluting tank and the diluted blood producing unit and configured to perform blood measurement by causing a current to flow between the first and second electrodes when diluted blood supplied to the first chamber by the diluted blood producing unit is contained in the first chamber and a diluting solution is contained in the second chamber,
   wherein the controller is configured to initiate an electrolysis cleaning process and to apply a voltage between the first and second electrodes when the diluting solution is contained in both of the first and second chambers.

2. The blood measuring apparatus according to claim 1, further comprising an inputting unit through which a washing instruction is to be given, wherein when the controller receives the washing instruction, the controller produces a washing solution and performs washing by using the produced washing solution.

3. The blood measuring apparatus according to claim 1, wherein the controller detects a time when washing is necessary, and when the controller detects the time, the controller produces a washing solution and performs washing by using the produced washing solution.

4. The blood measuring apparatus according to claim 1, wherein the controller produces a washing solution and performs washing by using the produced washing solution at a predetermined time.

5. The blood measuring apparatus according to claim 1, wherein a washing solution includes a first washing solution produced in the first chamber and a second washing solution produced in the second chamber, and the controller performs washing using one of the first washing solution and the second washing solution.

6. The blood measuring apparatus according to claim 1, wherein the controller sets at least one of an applied voltage, a time length of voltage, and a polarity.

7. A method of performing an electrolysis cleaning process to clean at least an aperture through which first and second chambers communicate with each other in a blood measuring unit, the method comprising:

performing blood measurement by causing a current to flow between first and second electrodes which are disposed respectively in the first and second chambers, when diluted blood is contained in the first chamber and diluting solution is contained in the second chamber;

applying a voltage between the first and second electrodes when diluting solution is contained in both of the first and second chambers to produce, in the first and second chambers, washing solution for cleaning the at least aperture.

8. The method of claim 7, further comprising:

providing a controller and an inputting unit through which a washing instruction is to be given, wherein when the controller receives the washing instruction, the controller produces a washing solution and performs washing by using the produced washing solution.

9. The method according to claim 7, further comprising:
providing a controller; and
detecting a time when washing is necessary using the controller, and when the controller detects the time, producing a washing solution and washing by using the produced washing solution.

10. The method according to claim 7, further comprising:
a controller configured to produce a washing solution; and
performing washing by using the produced washing solution at a predetermined time.

11. The method according to claim 7, further comprising:
providing a controller and a washing solution including a first washing solution located in the first chamber and a second washing solution located in the second chamber; and
washing, at an instruction of the controller, using one of the first washing solution and the second washing solution.

12. The method according to claim 7, further comprising:
providing a controller; and
setting at least one of an applied voltage, a time length of voltage, and a polarity via the controller.

* * * * *